(12) United States Patent
Ohneck (10) Patent No.: US 11,007,373 B1
(45) Date of Patent: May 18, 2021

(54) PHOTOBIOSTIMULATION DEVICE AND METHOD OF USING SAME

(76) Inventor: James Andrew Ohneck, Solon, OH (US)

( * ) Notice: Subject to any disclaimer, the term of this patent is extended or adjusted under 35 U.S.C. 154(b) by 0 days.

(21) Appl. No.: 10/291,738

(22) Filed: Dec. 20, 2002

(51) Int. Cl.
*A61N 5/06* (2006.01)

(52) U.S. Cl.
CPC .................................... *A61N 5/06* (2013.01)

(58) Field of Classification Search
CPC ............................. A61B 18/18; A61B 18/20
USPC ......................... 128/898; 606/9; 607/88–94
See application file for complete search history.

(56) References Cited

U.S. PATENT DOCUMENTS

| | | |
|---|---|---|
| 3,769,963 A | 11/1973 | Goldman et al. |
| 3,900,034 A | 8/1975 | Katz et al. |
| 4,069,823 A | 1/1978 | Isakov et al. |
| 4,396,285 A | 8/1983 | Presta et al. |
| 4,573,465 A | 3/1986 | Sugiyama et al. |
| 4,573,467 A | 3/1986 | Rich et al. |
| 4,640,283 A | 2/1987 | Sawa et al. |
| 4,669,839 A | 6/1987 | Muchel |
| 4,671,285 A | 6/1987 | Walker |
| 4,724,835 A | 2/1988 | Liss et al. |
| 4,785,811 A * | 11/1988 | Mori ............................. 607/93 |
| 4,854,320 A | 8/1989 | Dew et al. |
| 4,930,504 A | 6/1990 | Diamantopoulos et al. |
| 4,931,053 A | 6/1990 | L'Esperance, Jr. |
| 4,966,144 A | 10/1990 | Rochkind et al. |
| 4,984,242 A | 1/1991 | Scifres et al. |
| 5,002,051 A | 3/1991 | Dew et al. |
| 5,021,452 A | 6/1991 | Labbe et al. |
| 5,049,147 A | 9/1991 | Danon |
| 5,050,597 A | 9/1991 | Daikuzono |
| 5,112,328 A | 5/1992 | Taboada et al. |
| 5,147,349 A | 9/1992 | Johnson et al. |
| 5,150,704 A | 9/1992 | Tatebayashi et al. |
| 5,161,526 A | 11/1992 | Hellwing et al. |
| 5,196,004 A | 3/1993 | Sinofsky |
| 5,259,380 A | 11/1993 | Mendes et al. |
| 5,290,273 A | 3/1994 | Tan |
| 5,312,395 A * | 5/1994 | Tan et al. ........................ 606/9 |
| 5,312,396 A | 5/1994 | Feld et al. |
| 5,346,488 A | 9/1994 | Prince et al. |

(Continued)

OTHER PUBLICATIONS

Ethne L. Nussbaum, "Low-Intensity Laser Therapy for Benign Fibrotic Lumps in the Breast Following Reduction Mammaplast", source: Physical Therapy vol. 79, No. 7, Jul. 1999.

*Primary Examiner* — Aaron F Roane
(74) *Attorney, Agent, or Firm* — Dominic A. Frisina (57) ABSTRACT

An apparatus and method for directing light radiation onto an intended treatment area to create an optimum power density in order to promote photobiostimulation to aid in the healing of damaged tissue in the intended treatment area. The apparatus includes a light emitting element capable of simultaneously emitting multiple beams of light radiation have multiple wavelengths onto a target surface area. A hand guide protects the hand of a user from being irradiated and a distance control element ensures a optimum distance between the light emitting element and the target surface area. The apparatus includes multiple layers of safety features to prevent thermal damage of the target surface area and to prevent leakage of the non-focussed light radiation into the atmosphere. The method includes steps for using the apparatus of the present invention.

22 Claims, 9 Drawing Sheets

(56) References Cited

U.S. PATENT DOCUMENTS

| | | |
|---|---|---|
| 5,409,482 A | 4/1995 | Diamantopoulos |
| 5,445,146 A | 8/1995 | Bellinger |
| 5,464,436 A | 11/1995 | Smith |
| 5,520,679 A | 5/1996 | Lin |
| 5,527,350 A | 6/1996 | Grove et al. |
| 5,540,676 A | 7/1996 | Frieberg |
| 5,599,342 A * | 2/1997 | Hsia et al. .................. 606/9 |
| 5,616,140 A | 4/1997 | Prescott |
| 5,628,744 A | 5/1997 | Coleman et al. |
| 5,707,403 A | 1/1998 | Grove et al. |
| 5,728,090 A | 3/1998 | Martin et al. |
| 5,735,844 A * | 4/1998 | Anderson et al. ............ 606/9 |
| 5,743,901 A * | 4/1998 | Grove et al. ................ 606/9 |
| 5,755,752 A | 5/1998 | Segal |
| 5,814,008 A | 9/1998 | Chen et al. |
| 5,824,023 A * | 10/1998 | Anderson .................. 607/88 |
| 5,843,143 A * | 12/1998 | Whitehurst ............ A61N 5/062 250/504 R |
| 5,925,034 A | 7/1999 | Buckley et al. |
| 5,951,596 A | 9/1999 | Bellinger |
| 5,968,033 A | 10/1999 | Fuller et al. |
| 5,968,034 A | 10/1999 | Fullmer et al. |
| 5,993,442 A | 11/1999 | Omori |
| 6,033,431 A | 3/2000 | Segal |
| 6,048,359 A | 4/2000 | Biel |
| 6,063,108 A | 5/2000 | Salansky et al. |
| 6,143,019 A | 11/2000 | Motamedi et al. |
| 6,235,015 B1 | 5/2001 | Mead, III et al. |
| 6,251,102 B1 | 6/2001 | Gruzdev et al. |
| 6,261,310 B1 * | 7/2001 | Neuberger et al. ............ 607/89 |
| 6,267,779 B1 | 7/2001 | Gerdes |
| 6,273,885 B1 | 8/2001 | Koop et al. |
| 6,312,451 B1 | 11/2001 | Streeter |
| 6,350,261 B1 | 2/2002 | Domankevitz et al. |
| 6,370,422 B1 | 4/2002 | Richards-Kortum et al. |
| 6,425,873 B1 | 7/2002 | Marchitto et al. |
| 6,817,997 B2 * | 11/2004 | Furuno etal. ................ 606/9 |
| RE38,670 E * | 12/2004 | Asah et al. .................. 606/9 |
| 6,942,658 B1 * | 9/2005 | Rizoiu et al. ................ 606/16 |
| 2002/0002391 A1 | 1/2002 | Gerdes |
| 2002/0010500 A1 | 1/2002 | Chen |
| 2002/0065512 A1 | 5/2002 | Fjield et al. |
| 2002/0068924 A1 | 6/2002 | Sinofsky |
| 2002/0068926 A1 * | 6/2002 | Ota et al. .................... 606/9 |
| 2002/0107509 A1 * | 8/2002 | Neuberger et al. ............ 606/9 |
| 2002/0111610 A1 | 8/2002 | Nordquist |
| 2002/0165525 A1 * | 11/2002 | Nakamura ............ A61B 18/22 606/4 |

\* cited by examiner

PHOTOBIOSTIMULATION DEVICE AND METHOD OF USING SAME

BACKGROUND

1. Field of the Present Invention

The present invention relates generally to the use of light radiation for the treatment of living organisms. More specifically, the present invention relates to a portable apparatus and a method for applying light radiation to a target surface area on the skin of a patient in order to aid in the recovery of damaged cells of an intended treatment area at or below the target surface area without further damaging the intended treatment area.

2. Description of the Related Art

The use of light radiation for medical purposes is well known in the art. For example, light radiation, such as laser light, has been used for some time in surgical procedures such as cutting tissue, vaporizing tissue, cauterizing, and the like. An advantage of laser light is that optical energy can be delivered to an intended treatment area in a precise, well defined location and at a predetermined, limited energy levels. Recently, it has been found that laser light has many beneficial therapeutic advantages when used as an aid in the healing of damaged tissue. When a living cells interacts with light radiation for a given amount of time, a photochemical process takes place, known as photobiostimulation, which process has been found to aid in the recovery and healing of the damaged cells. It has been found that photobiostimulation occurs in tissue where light having a certain power density is created by the application of light radiation over a given time, which translates into energy density. Different forms of tissue react to different amounts of power density in order for photobiostimulation to be effective. Application of laser light for a pre-determined amount of time to achieve an optimum power density at an intended treatment area has been found to, among other things, reduce or eliminate chronic pain, promote healing of wounds, and reduce inflammation both at the surface of a patient's skin and internally.

In general, tissue irradiated with laser light either reflects, transmits, or absorbs the light. For a given tissue type, laser light having a certain wavelength may propagate through the tissue substantially obstructed, or may be almost entirely absorbed. It is generally preferred that the laser light be essentially transmissive through tissues which are not to be affected, and absorbed by tissues which are to be affected. For example, when applying laser radiation to a region of tissue permeated with water or blood, it is desired that the optical energy not be absorbed by the water or blood, thereby permitting the laser energy to be directed specifically to the tissue to be treated.

It has been found however, that a given type tissue will reflect, transmit or absorb light as a function of the wavelength of the light directed at the tissue. Specifically, green wavelength laser light is substantially absorbed at the surface of the skin making it useful in surface wound healing whereas red wavelength laser light is substantially reflected at the surface of the skin making it useful for identifying the skin of the patient directly above the intended treatment area, known as the target surface area. It has also been found that infrared light (not visible to the human eye) can penetrate deeply into human tissue making it useful for treatment of areas beneath the surface of the skin.

However, due to the varied absorption characteristics of tissue the depth to which a given wavelength of light will penetrate a particular tissue may be dependent on the degree to which the tissue is transmissive at the given wavelength. In living tissue, water is a predominant component and has, in the infrared portion of the electromagnetic spectrum, an absorption band determined by the vibration of water molecules. In the visible portion of the spectrum, there exists absorption due to the presence of hemoglobin. Further, the scattering coefficient in living tissue is also a dominant factor. As such, even with infrared light a substantial portion of the light directed at an intended treatment area beneath the surface of the skin will not reach the intended treatment area thereby not achieving a power density required for effective photobiostimulation. Therefore, there exists a need to effectively promote photobiostimulation to damaged tissue beneath the surface of the skin.

To overcome the natural absorption characteristics of tissue high power lasers have been used in order to increase the amount of light radiation directed at the intended treatment area, either on the surface of the skin or internally. High power lasers can a deliver large amount of light radiation in a short period of time over a wide target surface area. A drawback of using any form of light, however, is that heating will naturally occur on any surface where the light is directed. Particularly true with laser light, heating, or overheating, of anatomical areas can become a problem. Overheating is specifically an issue when attempting to use laser light during a long exposure period to aid in the recovery or healing of damaged cells beneath the surface of the skin. Even though tissue does have a heat dispersion coefficient, the use of a high power laser over a certain time period can lead to the accrual of more heat than can be dispersed naturally. Eventually the intended treatment area can be thermally damaged. As such, there is a risk in using high power lasers in that a high power laser can achieve a required power density for photobiostimulation of an intended treatment area but extended exposure to high power laser light can cause burning of the intended treatment area, delaying healing time, and defeating the purpose of the treatment. Therefore, there exists a need for a laser capable of quickly delivering a high power density over a wide surface area without thermally damaging the intended treatment area or the target surface area, if they differ.

To overcome the drawbacks of high power laser for treatment of internal intended treatment areas, use of Low Level Laser Therapy ("LLLT") has been implemented LLLT typically implements a laser power level not greater than 1,000 milliwatts ("mW") and includes a single wavelength. However, LLLT also has drawbacks in that it may require long treatment periods in order to achieve a predetermined power density for effective photobiostimulation to occur LLLT often requires the use of a collimated light beam providing an extremely small focal point of the laser. Use of collimated beams limits the applicable surface area treated by the laser during any one application which will cause long application periods as the laser energy is swept across the entire intended treatment area. For intended treatment areas that are small, such as the wrist or ankle, treatment sessions may not run long. However, for larger intended treatment areas, such as a hip or back, use of focussed or collimated laser light devices requires longer treatment periods in order to effectively apply the laser energy to the entire intended treatment area. In addition, it has been found that LLLT often requires frequent sessions over a long time span.

Therefore, there exists a need for a laser capable of effectively delivering a high power density across large and small intended treatment areas without the need for frequent long treatment sessions over an extended treatment period.

A number of prior art devices have focused on the use of lasers for such treatments having a wavelength in the near infrared range. For example, U.S. Pat. No. 5,445,146 issued to Bellinger discloses the use of a Nd:YAG laser having a fundamental wavelength of 1064 nanometers with a power level between 100 milliwatts and 800 milliwatts. The Nd:YAG laser is traditionally a pumped laser, excited by an external light source. Such lasers are typically rather cumbersome, relatively expensive, and the output power is somewhat difficult to control. In addition, such lasers are only available with light output at specific wavelengths.

U.S. Pat. No. 5,925,034, issued to Buckely et al., discloses a method of treating a living tissue target of skin using an optical fiber bundle to apply radiation to the target, where the optical fiber bundle includes a stabilization member that contacts the skin. However, there are occurrences where it is desirable to aid the healing of an intended treatment area which lies beneath the surface of the skin where an open wound may exist. In these cases, multiple wavelengths of light are desirable in addition to a device that is capable of delivering the light radiation without contacting the wound.

U.S. Pat. No. 6,267,779, issued to Gerdes discloses a therapeutic laser apparatus including at least two wands connected to a controller and radiation source via fiber optic cables. This device disadvantageously requires the use of both hands by the technician.

U.S. Pat. No. 6,312,451 issued to Streeter discloses a therapeutic laser apparatus that includes a handheld probe with laser diodes located in the probe. However, this apparatus requires substantial skin contact and only does not include distance control safety features.

It has been found that the response of tissue to an exposure to light varies based on the wavelength, intensity, and duration of the exposure. In order to achieve a desired power density at an intended treatment area, either on the surface of the skin or internally, and the exposure of the intended treatment area must be tailored to, among other things: a) the particular tissue receiving treatment; b) the desired depth of penetration into the tissue for each wavelength of light; and c) the degree of stimulation required.

In light of the foregoing there exists a need for a photobiostimulation device capable of quickly delivering a high power density and maintaining a consistent beam diameter over a wide surface area without thermally damaging the intended treatment area or the target surface area, if they differ.

There also exists a need for a photobiostimulation device capable of effectively delivering a high power density across large and small intended treatment areas without the need for frequent long treatment sessions over an extended treatment period.

Further, there exists a need for a photobiostimulation device capable of controlling surface power density while providing deep penetration of light radiation in a small portable inexpensive device without power of heat distribution issues.

SUMMARY OF THE INVENTION

Accordingly, the present invention is directed to a photobiostimulation device and method of using same that substantially alleviates one or more of the problems arising from the limitations and disadvantages of the related art.

Additional features and advantages of the invention will be set forth in the description as follows, and in part will be apparent from the description or may be learned by practicing the invention. The objectives and other advantages of the invention will be realized and attained by the method and apparatus particularly pointing out in the written description and the claims hereof together with the appended drawings.

To achieve these and other advantages, and in accordance with the purpose of the invention, as embodied and broadly described in general and in a first aspect the invention features a photobiostimulation device including a light wave emitting element capable of directing the light waves over a target surface area of a patient in order to achieve a predetermined target surface area power density, a distance control element linked to the light emitting element, the distance control element being structured and arranged to maintain a predetermined distance between the light emitting element and the target surface area.

Preferred embodiments of the invention may include one or more of the following features including a laser power source optically connected to the light emitting element, the laser power source capable of creating laser light in the visible spectrum and delivering the laser light to the light emitting element, an infrared power source optically connected to the light emitting element, the infrared power source capable of creating infrared light and delivering the infrared light to the light emitting element. The laser power may be capable of emitting laser light having a power of about 25 watts where the laser light may be in the red visible spectrum. The infrared power source may be capable of emitting infrared light having a power of about 25 watts The predetermined target surface area power density may be between about 50 $mW/cm^2$ and about 25,000 $mW/cm^2$. The target surface area may be any shape, such as a square or a circle, where a circle may have a diameter between about 0.5 cm and about 10 cm. The light emitting element is capable of emitting light in pulsed or continuous wave.

The preferred embodiment may include a processor where the processor may be programmable to store patient data and to monitor operation parameters of the device. The preferred embodiment may also include a hand guide element connected to the light emitting element where the hand guide may be structured and arranged to inhibit the emitted light from contacting a control hand of a user. A portion of the hand guide may be made of a translucent material.

The preferred embodiment may also include a light sensing element, the light sensing element sensing emitted light reflected from the target surface area and sending a distance signal to the processor.

In other embodiments there may be included an adjustable spot size releasably connected to the light emitting element, where the spot size adjuster may include threaded portion and an adjustable screw. Manipulation of the screw may selectively maintain a pre-determined distance between the target surface area and the light emitting element.

In other embodiment of the present invention there may be included a focusing element where the focussing element may focus the emitted laser and infrared light onto the target surface area. The focussing element may include a shutter. In other embodiments the focussing element may include a lens where the lens may be optically coated. Further the lens may be a collimating lens.

In still other embodiments the present invention may include a wrap where the wrap may have a matrix of single optical fibers that converge into a single connector, which may be optically connected to the light emitting element to deliver a plurality of beams of light to the target surface area.

In yet another embodiment of the present invention there may be included an automated dithering element connected to the light emitting element where the dithering element may be capable of directing the laser light and the infrared light onto the target surface area in a predetermined pattern.

In another general aspect, the present invention may be a photobiostimulation device including a light emitting element capable of simultaneously emitting multiple beams of light having multiple wavelengths, wherein at least one beam of light is beam is in the visible red spectrum and at least one beam is infrared light and a distance control element linked to the light emitting element, where the distance control element being structured and arranged to maintain a predetermined distance between the light emitting element and a target surface area such that when the infrared light is emitted from the light emitting element and directed at a target surface area having a diameter between about 0.5 cm to about 10.0 cm, said infrared light is capable of achieving a target surface area power density between about 50 mW/cm$^2$ and about 2,500 mW/cm$^2$.

In another general aspect, the present invention may be a photobiostimulation device for treating an intended treatment area of a patient by directing a beam of infrared light to a target surface area on the skin of the patient, where the device includes a light emitting element capable of simultaneously emitting multiple beams of light having multiple wavelengths, the light emitting element emitting at least one beam of infrared light directed at the target surface area of the patient to achieve a pre-determined target surface area power density, a hand guide connected to the light emitting element, the hand guide, structured and arranged to prevent the emitted light from contacting a user's hand during treatment of the patient, and a distance control element linked to the light emitting element, where the distance control element being structured and arranged to maintain a predetermined distance between the light emitting element and the target surface area in order to maintain the predetermined surface area power density.

In still another general aspect, the present invention may include a photobiostimulation device having a light emitting element comprising power source capable of generating laser light having a power between 50 micro watts and 25 watts and a fiber optic delivery element capable of simultaneously emitting a plurality of laser light having multiple wavelengths, a processor for controlling the fiber optic delivery element, where the processor is electronically linked to the light emitting element and is programmed to monitor the power and wavelength of the laser light, a lens attached to the fiber optic delivery element, where the lens is capable of directing the laser light onto a target surface area having a diameter of between about 0.5 cm to about 10 cm, and a laser activation element connected to the fiber optic delivery element, the laser activation element comprising a switch control button operable by a user to selectively activate the power source and to regulate the lens to focus the laser light onto the target surface area.

This embodiment of the present invention may include a piezoelectric device operable by the user by actuation of the switch control button in order to focus of the lens to achieve a desired target surface area power density over a target surface area having a diameter between about 0.5 cm and about 10 cm.

In still another general aspect, the present invention may include a photobiostimulation device having a laser power source, where the laser power source emitting laser light and having a first cable extending therefrom wherein the laser light is carried from the first power source, an infrared power source, where the infrared power source emitting infrared light having a second cable extending therefrom wherein the infrared light is carried from the second power source, a dual optical cable having an entry port and an exit port, an optical coupler, having a proximal end connected to the first and second cables and a distal end connected to the entry port of the dual optical cable, where the optical coupler receives the laser and the infrared light via the first and second cables respectively and where the optic coupler couples the laser and the infrared light into a coupled light signal and transmits the coupled light signal to the entry port of the dual optical cable, a light emitting element having a receiving end and an emitting end, the light emitting element coupled to the exit port of the dual optical cable where the light emitting element receives the coupled light signal via the exit port of the dual optical cable at a receiving end of the light emitting element and emits the laser light and infrared light simultaneously from the emitting end, a processor linked to the laser light power source, the infrared light power source and the light emitting element, the processor being programmed to control the power level and a wavelength of each emitted wave of light, and a distance control element structured and arranged to maintain an optimum distance between the light emitting element and a target surface area in order to achieve a predetermined target surface area power density.

Features of this embodiment may include a hand guide element positioned proximal to the emitting end of the light emitting element, the hand guide being structured and arranged to inhibit the infrared light or the laser light from contacting a hand of a user.

Other features in the present invention may also include a spot size adjuster releasably connected to the light emitting element, wherein the spot size adjuster may include comprises a threaded portion and an adjustable screw, where manipulation of the screw selectively maintains a predetermined distance between the target surface area and the light emitting element.

In other embodiments the present invention may include an optical detector, where the optical detector detects laser light reflected from the target surface area and based upon the amount of laser light detected by the optical detector, the device may selectively modify the power level of the infrared laser to maintain the predetermined target surface area power density.

In yet another general aspect, the present invention includes a method for treating an intended treatment area of a patient with a photobiostimulation device having a light emitting element capable of directing a beam of light radiation waves to a target surface area on the skin of the patient above the intended treatment area, where the method may include the steps of determining a target surface area power density according to the patient diagnosis and medical history, determining the size of the target surface area to be treated, the power level and the treatment time from the patient diagnosis and medical history and the determined optimum target surface area power density, providing a light emitting element capable of emitting light radiation waves having a selectable wavelength and simultaneously emitting a targeting beam of a visible wavelength of light, adjusting the distance between the light emitting element in order to obtain the predetermined power density across the target surface area, and directing the light radiation onto the target surface area for the determined treatment time in order to obtain the predetermined power density across the target surface area. An embodiment of the present invention may include a wavelength of the emitted light radiation between about 530 nm and about 1064 nm and wherein the wavelength of the emitted targeting beam may be between 530 nm and 700 nm. The light radiation can be either pulse wave or continuous wave capable of being emitted at up to about 10,000 cycles per second. The present invention may include a treatment time up to about 7200 seconds.

In still another general aspect, the present invention may include a system for photobiostimulation of a target surface area of a patient, where the target surface area is on located on the skin of the patient above the intended treatment area, the system having a unified portable housing having a power supply connected to a microprocessor controller and a light generating power source capable of simultaneously generating multiple selected wavelengths of light, an optical cable optically connected to the light generating power source, the optical cable capable of simultaneously transmitting multiple selected wavelengths of light, a light emitting element optically connected to the optical cable and linked to the microprocessor control, the light emitting element comprising switch operable by a single hand of a user, the switch being operable to actuate the light emitting element to simultaneously emit multiple selected wavelengths of light directed onto the target surface area having a diameter of between about 0.5 cm and about 10 cm, and a distance control element linked to the light emitting element and the microprocessor control, the distance control element structured and arranged to maintain and optimum distance between the light emitting element and the target surface area, wherein, the microprocessor controller is programmed to determine the distance between the light emitting element and the target surface area and based on the distance between the light emitting element and the target surface area control and selectively modify the power and wavelength of the emitted light, a treatment time of the target surface area and the diameter of the target surface area in order to achieve a target surface area power density of between about 50 mW/cm$^2$ and about 2,500 mW/cm$^2$.

The above advantages and features are of representative embodiments only, and are presented only to assist in understanding the invention. It should be understood that they are not to be considered limitations on the invention as defined by the claims, or limitations on equivalents to the claims. Additional features and advantages of the invention will become apparent from the drawings, the following description, and the claims.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the figures, wherein:

DETAILED DESCRIPTION

The present invention provides a new and useful apparatus that provides a substantially contact free treatment to manage a patient's pain using laser energy to selectively penetrate a predetermined anatomical surface area, the intended treatment area, to a desired depth without overheating the intended treatment area or the target surface area above the intended treatment area, if they differ.

As discussed above, it has been found that light radiation directed onto living tissue induces photobiostimulation which aids in the recovery and healing of damaged tissue. However, in order to promote photobiostimulation it is necessary to deliver a certain amount of power density to the intended treatment area over a predetermined amount of time.

Power density can be determined from the following equation:

Power Density (mW/cm$^2$)=Power (mW)/$\Pi \times r^2$, where Power is an expression of the power of the laser source and r is the radius of the target surface area.

Power density expressed over a given time is know as the Energy Density, which is expressed by the following equation:

Energy Density (Joules)=Mean Power (W)×Time applied (sec.), where 1 Joule=1 W/sec.

Therefore, Energy Density is expressing the Power Density in terms of time as follows:

$$\text{Power Density (mW)} \times \text{Time (Sec)} = \frac{\text{Energy density }(J)}{\Pi \times r^2 \text{ (cm}^2\text{)}}$$

It has been found that the optimum power density can be achieved by maintaining a consistent beam diameter over the target surface area. This is primarily a function of the distance between the light emitting element, discussed below, and the target surface area. Additional factors including wavelength, type of radiation, anatomical characteristics of the target surface area and the skill of the technician operating the system will affect the beam diameter. It is preferable that a consistent beam diameter be maintained during the entire treatment session for best results.

Figure 1:
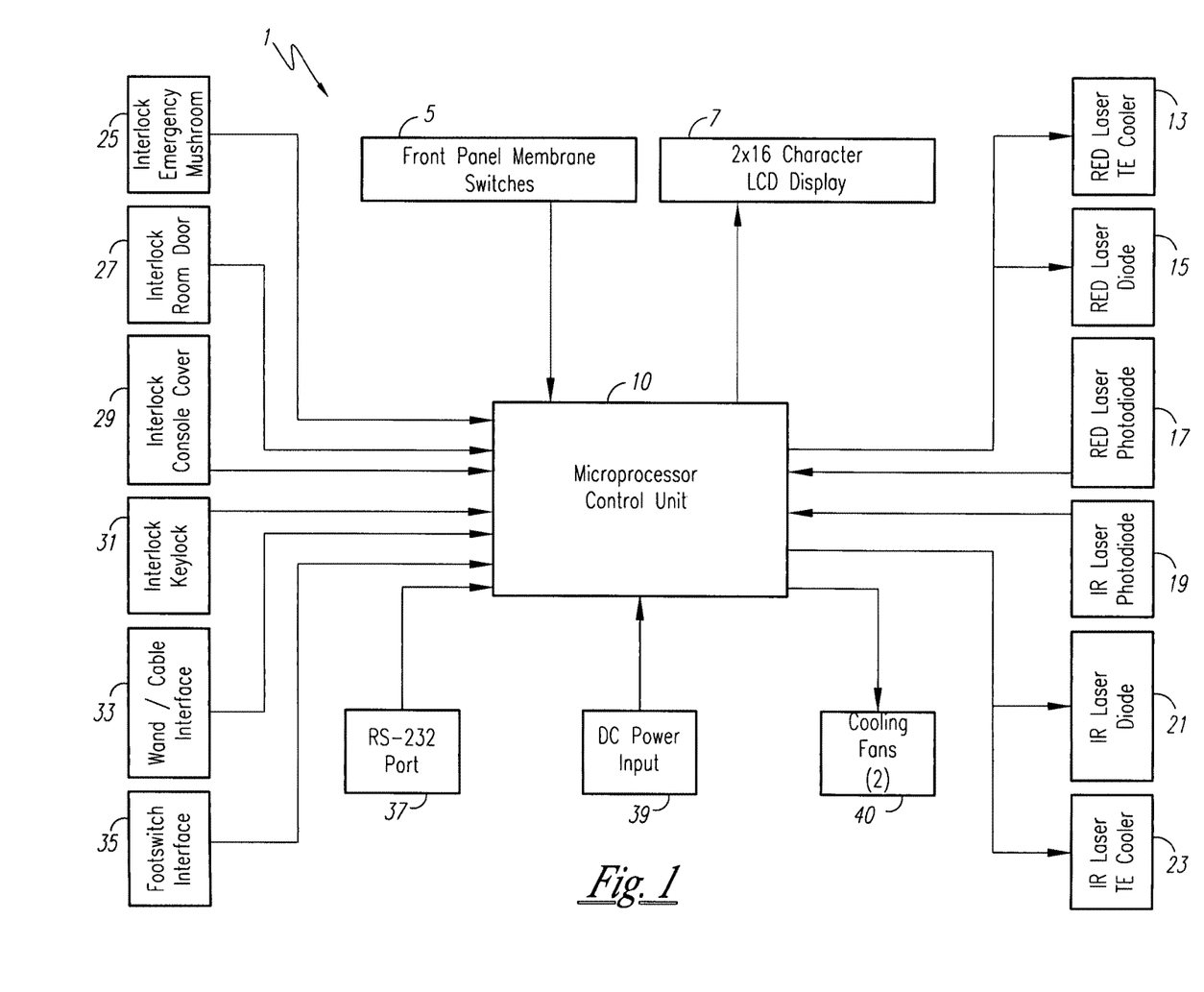
FIG. 1 shows a block diagram of the system according to the invention.

Referring now to FIG. 1 there is shown a block diagram of the photobiostimulation system 1 according to present invention. In the preferred embodiment there may be a microprocessor control unit 10 for controlling the various elements of system 1. System 1 may have front panel membrane switches 5 which are adaptable for user input. Such user input may be reflective of user ID, patient ID and medical data, treatment time, power and wavelength settings. Such user input may be displayed on display 7. Display 7 as shown can contain control buttons for setting the laser power, the treatment time, resetting the time, and for selecting various preset protocols for treatment.

System may include laser diodes 15 and 17. Laser photodiodes 13 and 19 may also be provided. Photodiodes 13 and 19 are typically photoelectric semiconductor devices for detecting and often measuring radiant energy, such as light. Thermal coolers 13 and 23 may be located proximal to the diodes and photodiodes, along with cooling fans 41, to maintain a consistent output through temperature fluctuations in the laser diodes and photodiodes. Although the preferred embodiment is described with a red laser and an infrared laser, those with ordinary skill in the art will understand that lasers in other areas of light spectrum may work as well as those described herein.

Port 37 may provide an interface with telephone or telephony connections in order to link with a personal computer, handheld device or other database. It will be understood that each of the devices can connect with system 1 via any conventional interface such as an RS-232 connection, Ethernet, radio frequency or infrared. Input 39 provides electrical power for the system, which may be either AC or DC. It will also be understood that system 1 can be used with DC power via a conventional battery back or AC power with any standard plug receptacle. At least one cooling fan 41 may be provided to extract heat from the interior of the system. Footswitch interface 35 may be provided for a foot switch (not shown) which can activate the laser and provide an additional level of safety for system 1. Cable interface 33 provides an interface juncture point for external optical cable 240 out of system 1.

System 1 may include multiple layers of safety features such as keylock 31, console cover interlock 29, room door interlock 27 and emergency button 25. Keylock 31 can be a conventional key and tumbler locking system having at least an "active" and "inactive" positions. When a key (not shown) is placed into keylock 31 and rotated to the active position system 1 can be activated. When keylock 31 is on the inactive position system 1 cannot be activated. It will be understood that keylock 31 may be any conventional key security system such as a combination lock, an electronic lock, a passcard lock, a fingerprint lock, or other user identification locking system. Console cover interlock 29 provides a deactivation mechanism should system 1 be activated and the chassis 100, discussed below, be openly accessible. Room door interlock 27 can be a safety lock connected to system 1 that monitors an entrance way in a treatment room in order to prevent retinal damage to individuals unknowingly entering the treatment room where system is being operated. The door safety interlock provides an output for a technician to connect a switch to the door such that if the door is opened during operation of system 1, the system will shut down. Emergency button 25 is a large safety button required by law to be placed on any device of this nature.

Figure 2:
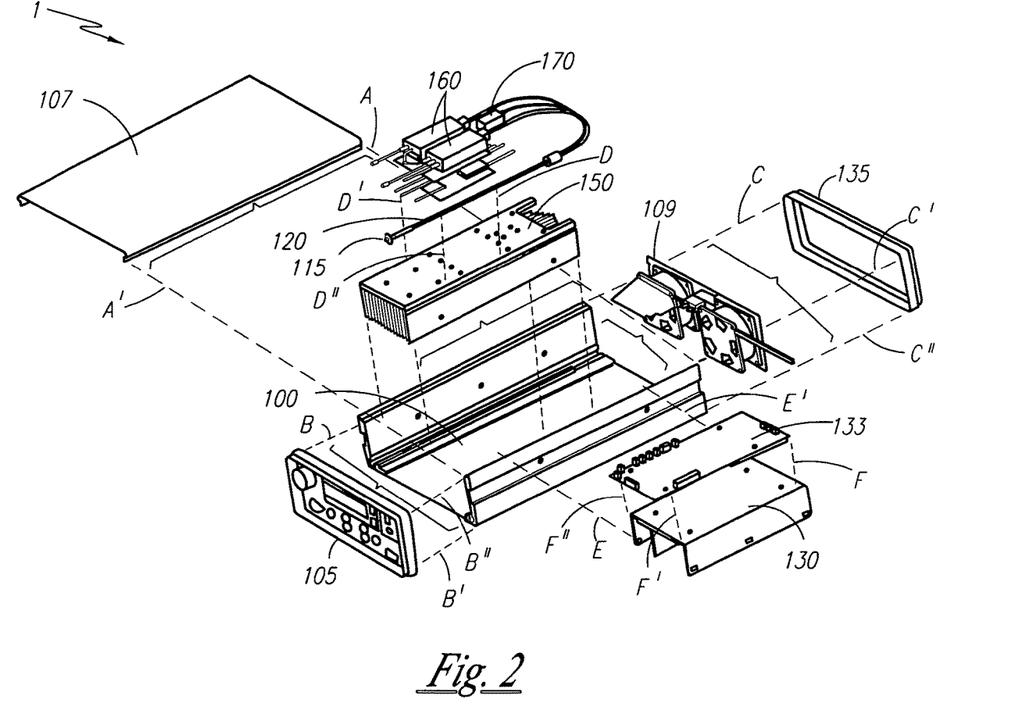
FIG. 2 shows an exploding view of an apparatus according to one embodiment of the invention.
Figure 3:
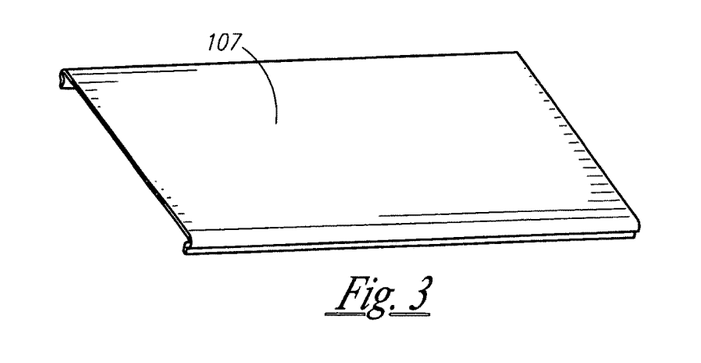
FIG. 3 shows a perspective view of the chassis cover of FIG. 2 according one embodiment of the invention.

FIG. 3. shows chassis cover 107 which preferably seals and electrically insulates the interior of system 1. Referring now to FIG. 2 there is shown an exploding view of the various components of system 1. System 1 includes a chassis 100 to provides the physical support for the components mounted internally. There may be a motherboard 133 where a processor can be located, such as the microprocessor control unit 10, that may contain the necessary software and hardware, such as a database, that may control system 1. Also included may be a medical grade power supply transformer 130 which may supply necessary power for driving the lasers 160 and 170, discussed below, and provide the power for the other circuitry of system 1. The medical grade power supply 130, such as those sold by Integrated Power Design, must meet certain emissions standards and electrical safety standards necessary for medical equipment. Rear panel 109 is affixed to chassis 100. Affixed on rear panel 109 there may be least one cooling fan 41. Preferably there are multiple cooling fans 41 as space will allow. In some embodiments, a first cooling fan 41 can be an input fan, and a second cooling fan 41 can be an output fan, both fans creating an airflow in system 1 to efficiently circulate cool air through the entirety of the system preventing the various components from overheating. Rear panel bezel 135 is connected to the rear of chassis 100 and preferably seals rear panel 109 securely to chassis 100 and electrically insulates system 1.

Figure 4:
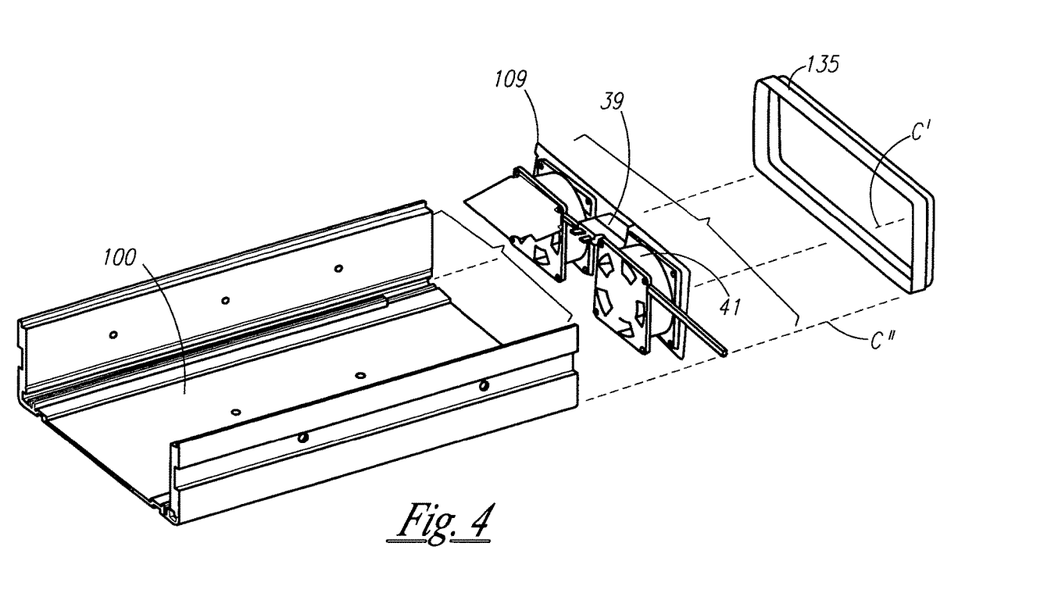
FIG. 4 is shows an exploding view of the chassis, rear interface and bezel of FIG. 2 according to one embodiment of the invention.
Figure 5:
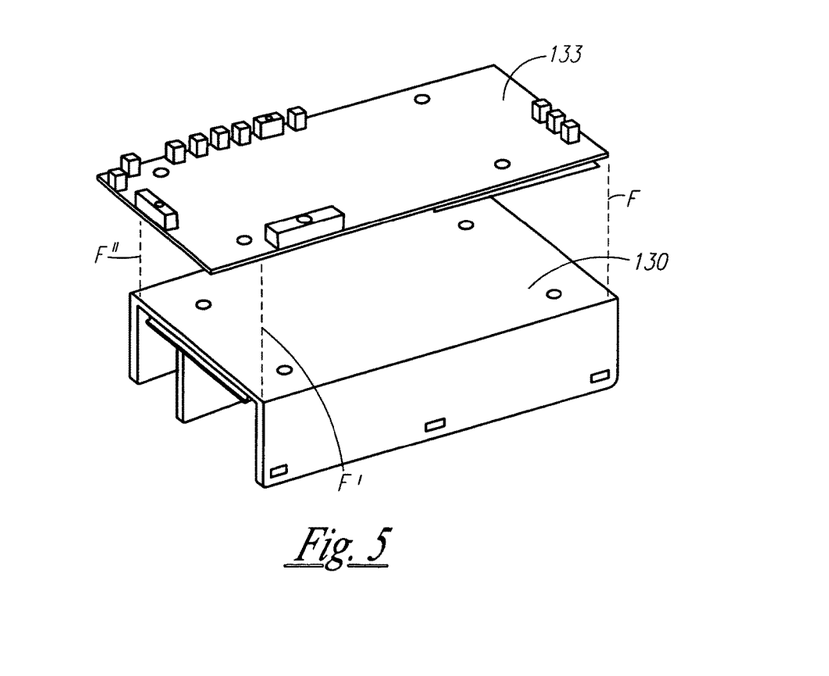
FIG. 5 shows an exploding view of the mother board and medical power supply of FIG. 2 according one embodiment of the invention.

Referring now to FIG. 4, chassis 100 is structured and arranged to support rear panel 109. As indicated above rear panel 109 preferably includes cooling fans 41. Also included on rear panel 109 is power input 39, which may be AC or DC. Bezel 135 seals rear panel 109 along lines C, C' and C". In FIG. 5 motherboard 133 is aligned with medical power supply 130 along lines F, F' and F".

Figure 6:
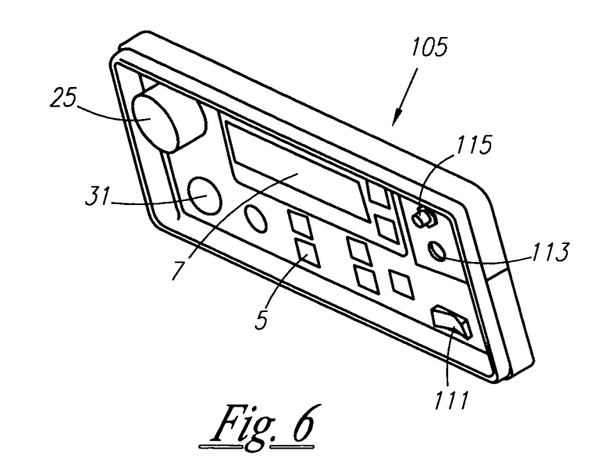
FIG. 6 shows a user interface element of FIG. 2. according to one embodiment of the invention.

FIG. 6 shows front panel 105 which includes an on/off button 111, input buttons 5 and display 7. As indicated above, input buttons 5 are provided so that a technician may input various operational settings and/or patient parameters. Further, input buttons can include a keyboard (not shown) that may allow the input of detailed information which can be shown on display 7. Front panel 105 preferably includes optical interface 115, discussed below, which provides an interface for external optical cable 240, also discussed below, with the internal components of system 1. As proper energy delivery to the injured area or biological material is critical for successful photobiostimulation, the light beam being emitted must provide a specific surface power density for a certain period of time depending on the type of tissue being treated. Therefore the user of the apparatus can vary the power settings, pulse settings and treatment via the microprocessor computer 10, hand held computing device or other programmable database.

Also included in panel 105 are numerous safety features including emergency button 25 and keylock 31. Safety interlock 113, which works in conjunction with external optical cable 240 and optical interface 115, prevents exposure of non-focussed light radiation to the atmosphere.

Figure 7:
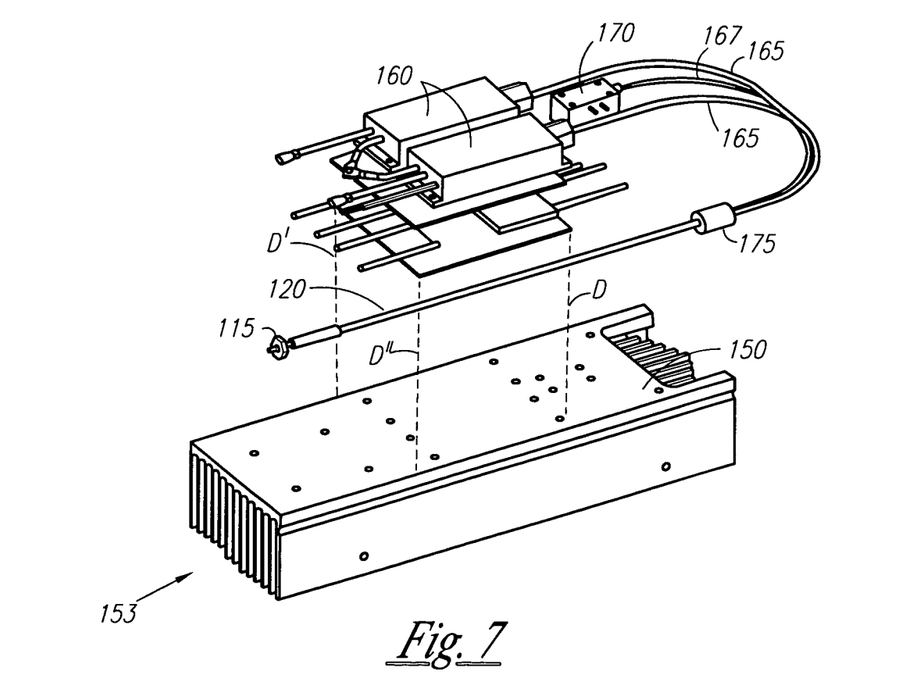
FIG. 7 shows an exploding view of the light radiation power source and heat sink of FIG. 2 according to one embodiment of the invention.

FIG. 7 shows an exploded close up view of laser sources 160 and 170 which are preferably aligned on top of heat sink 150 along lines D, D' and D". Laser sources 160 and 170 tend to create a large amount of heat which requires a close proximity to heat sink 150. Heat sink 150 preferably includes fins 153 for efficient distribution of heat when used in concert with cooling fans 41. Laser source 170 provides light radiation preferably in visible spectrum having a wavelength of about 635 nanometers to about 720 nanometers. Laser source 160 provides light radiation preferably in the infrared spectrum having a wavelength between about 800 to about 1064 nanometers. It will be understood that laser sources 160 and 170 may deliver light radiation in either pulsed or continuous waves. Laser sources 160 and 170 may contain multiple laser diodes of LED having different wavelengths enabling the therapist to select the appropriate wavelength for the treatment being rendered. The wavelength may be selected directly from front panel 105 which activates microprocessor controller 10. Alternatively, such determinations can be made automatically by microprocessor 10 upon technician entry of patient data or other treatment parameters. In other embodiments, system 1 can be operated remotely via an internet connection between a technician's office and a physician's office. In still other embodiments, system 1 can be operated via a hand held computing device. Such hand held devices are particularly advantageous in a clinical settings in the filed, such as when treating a patients in remote areas.

Light radiation is directed from laser source 160 via cables 165. Similarly, cable 167 carries light radiation from laser source 170. Cables 165 and 167 are connected to optical coupler 175, where light radiation from laser sources 160 and 170 are coupled into internal optical cable 120. As indicated above, it has been found that skin is highly transmissive with light in the infrared range and that an intended treatment area beneath the skin can be stimulated by such infrared light radiation. However because infrared light is beyond the visible spectrum for the unassisted eye of a user, it is important to "paint" the target surface area on the patient's skin with light in the visible spectrum. The light radiation in the visible spectrum is considered the "aiming beam." The light radiation that is in the infrared spectrum is the "treatment beam" for those intended treatment areas that are beneath the surface of the skin. Preferably, light radiation created from laser source 160 is used as the treatment beam where the light radiation from laser source 170, preferably in the red visible spectrum, is used as the aiming beam. It is important to have the aiming beam and the treatment beam synchronized so that when the user directs the visible aiming beam emitted from light emitting element 201 onto the target surface area the user is also directing the appropriate amount of invisible infrared spectrum treatment beam, which is simultaneously emitted from light emitting element 201, onto the target surface area.

Internal optical cable 120 is connected to optical connector 115 at the interface of front panel 105 (as shown in FIG. 6). Internal optical cable 120 carries the coupled light radiation from optical coupler 175 to the boundary of chassis 100 at panel 105.

Figure 8:
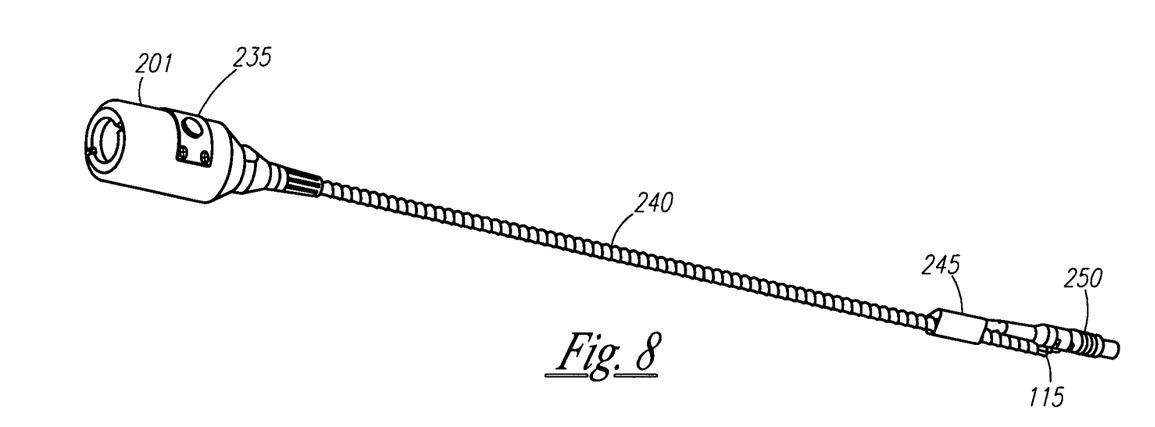
FIG. 8 shows a light emitting element according to one embodiment of the invention.
Figure 9:
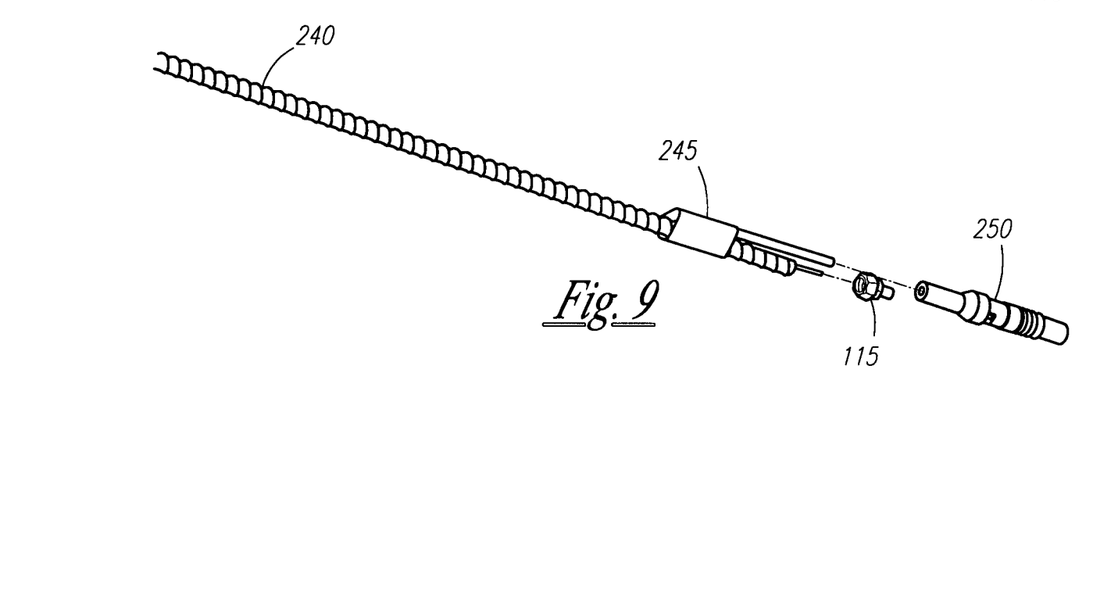
FIG. 9 shows an exploding view of a second end of the optical cable of FIG. 8 and an interface with the user interface element of FIG. 6 according to one embodiment of the invention.

Referring now to FIG. 8 there is shown light emitting element 201 having an activation switch 235. External optical cable 240 is optically connected to light emitting element 201 on one end. The other end of external optical cable 240 is connected to optical connector 115 at the interface of front panel 105 (front panel 105 is not shown in FIG. 8). As better shown in FIG. 9, also included on external optical cable 240 is bifurcation 245 which is connected to switch connector 250. Bifurcation 245 preferably carries electrical signals from activation switch 235 to switch connector 250. Switch connector 250 is preferably interfaced with front panel 105 at safety interlock 113. Disconnection of the external optical cable 240 from front panel 105 at optical connector 115 can lead to leakage of unfocussed light radiation into the atmosphere which can cause retinal damage to anyone unknowingly looking in the direction of system 1. As such, system 1 is structured and arranged such that switch connector 250 must be connected to safety interlock 113 and external optical cable 240 must be connected to optical connector 115 in order for system 1 to be activated. This feature provides an additional level of safety in case of accidental disconnection of external optical cable 240 from front panel interface 105. Additionally, various electrical connections can be provided to the light emitting element 201 via the interface between switch connector 250 and safety interlock 113. Optical connector 115 can be any conventional standard fiber optic connector including miniplug, biconci, D4, escon, face contact, FDDI, SC, MT-RJ, toslink plug, ST or preferably, as shown, Sub Miniature type A.

Figure 10:
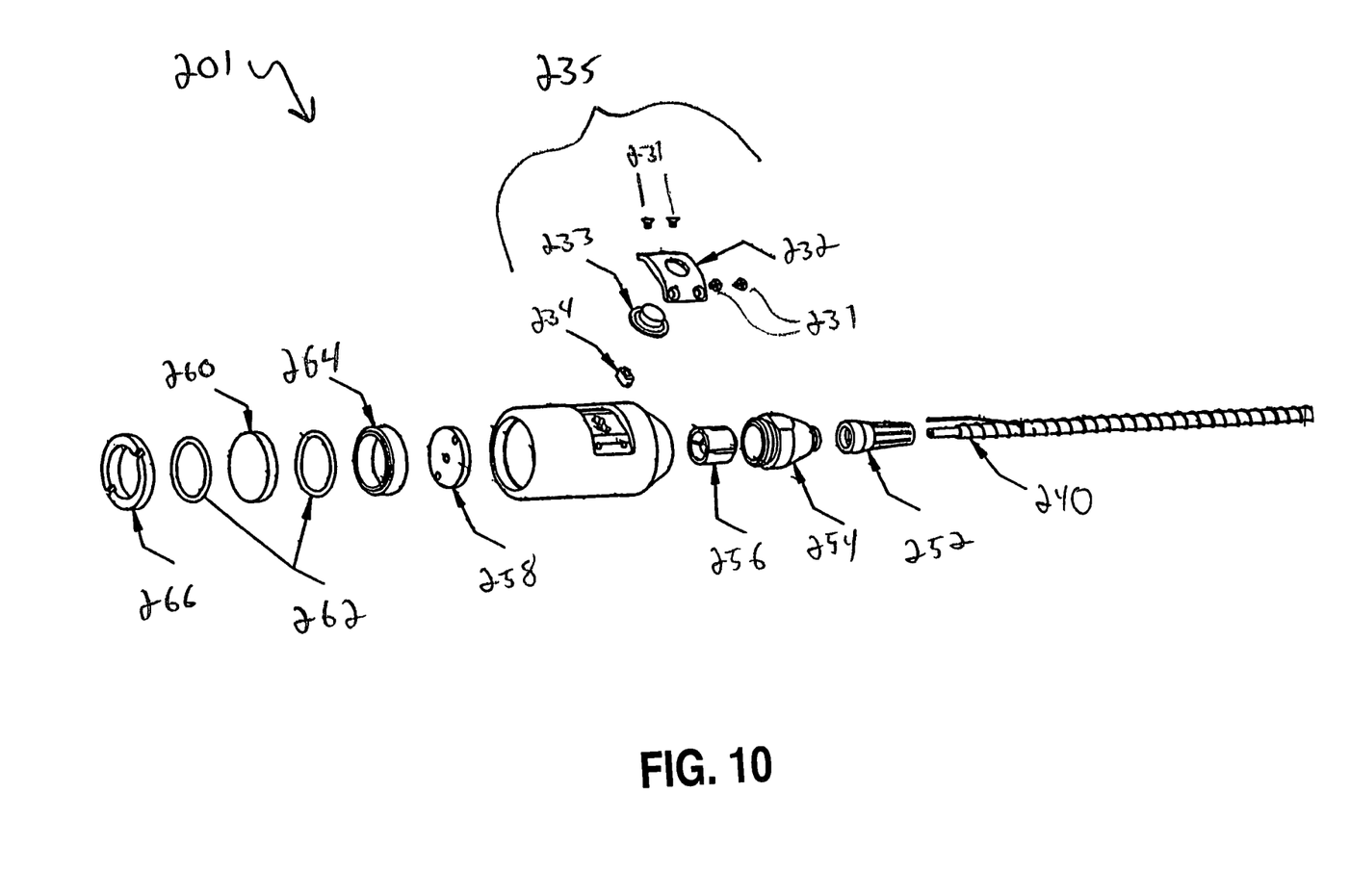
FIG. 10 shows an exploding view of the light emitting element and a first end of an optical cable of FIG. 8 according to one embodiment of the invention.

FIG. 10 shows an exploded view of the light emitting element 201. As can be seen external optical cable 240 is optically connected to light emitting element 201 via cable collet 256, collet housing 254 and strain relief 252. It has been found that this configuration prevents signal loss due to excess strain on the connection between the light emitting element 201 and the external optical cable 240. However, it is understood that other conventional configurations known in the art will suffice in this regard. Activation switch 235 can optionally include button retainer 232 which is secured to light emitting element 201 via screws 231 or similar fastening means. Activation switch 235 may also include button 233 and switch mechanism 234 which may be any conventional type of switching mechanism. In some embodiments, activation switch 235 may include a piezoelectric switch. The piezoelectric switch may be structured and arranged to selectively adjust the settings of the various parameters of system 1 in concert with microprocessor control 10. Where a user may selectively apply pressure upon the piezoelectric switch in a variety of directions to adjust the various operation parameters of system 1. In order to provide an additional level of safety, light emitting element 201 preferably cannot be activated without constant pressure applied to activation switch 235 by a user. Optionally, activation switch 235 may have a "click" mechanism with distinct on and off positions. Preferably the location of activation switch 235 is such that a user can operate light emitting element 201 comfortably with one hand.

Light emitting element 201 may also include focus alignment disk 258. The emitting end of light emitting element 201 is preferably sealed to the atmosphere so as to prevent harmful deposits from accumulating. Spacer 264 along with o-rings 262 and retainer 266 are configured to seal lens 260 to the emitting end of the light emitting element 201. In other embodiments, lens 260 can be configured with various light directing patterns to direct light radiation in selectable shapes, sizes and patterns onto a target surface area. In still other embodiments, lens 260 can be a shutter system operable to selectively modify the shape, size or pattern of light radiation directed onto a target surface area. Light radiation in the visible red spectrum is highly reflective off of skin tissue, where such reflected light can cause interface with and even damage light emitting element 201. As such, other embodiments of the present invention may include lens 260 configured with a camera-type iris to block out not only reflected light, but also background light radiation that may be harmful to the internal components of light emitting element 201. Optionally, lens 260 can be optically coated to block out light radiation having a wavelength of about 980 nanometers.

It has been found that non-collimated divergent beams of light radiation provide the best results. Collimated beams of light radiation create small target surface area imprints which are impractical for large intended treatment areas. Additionally, collimated light beams are typically used in surgical applications of lasers where a cutting tissue is necessary. Although there are embodiments of the present invention that can be effective with a collimated lens, it has been found that collimated beams of light radiation can quickly raise the temperature of the intended treatment area, beyond the normal heat dispersion rate of tissue, leading to thermal damage of the tissue.

It has been found that maneuvering light emitting element 201 in a circular motion in a predetermined pattern over the target surface area provides the best results in terms of achieving the optimum power energy density for photobiostimulation. This process of known as "dithering". As discussed above, it is preferable to have a skilled technician operate light emitting element 201 and system 1 in general.

Figure 11:
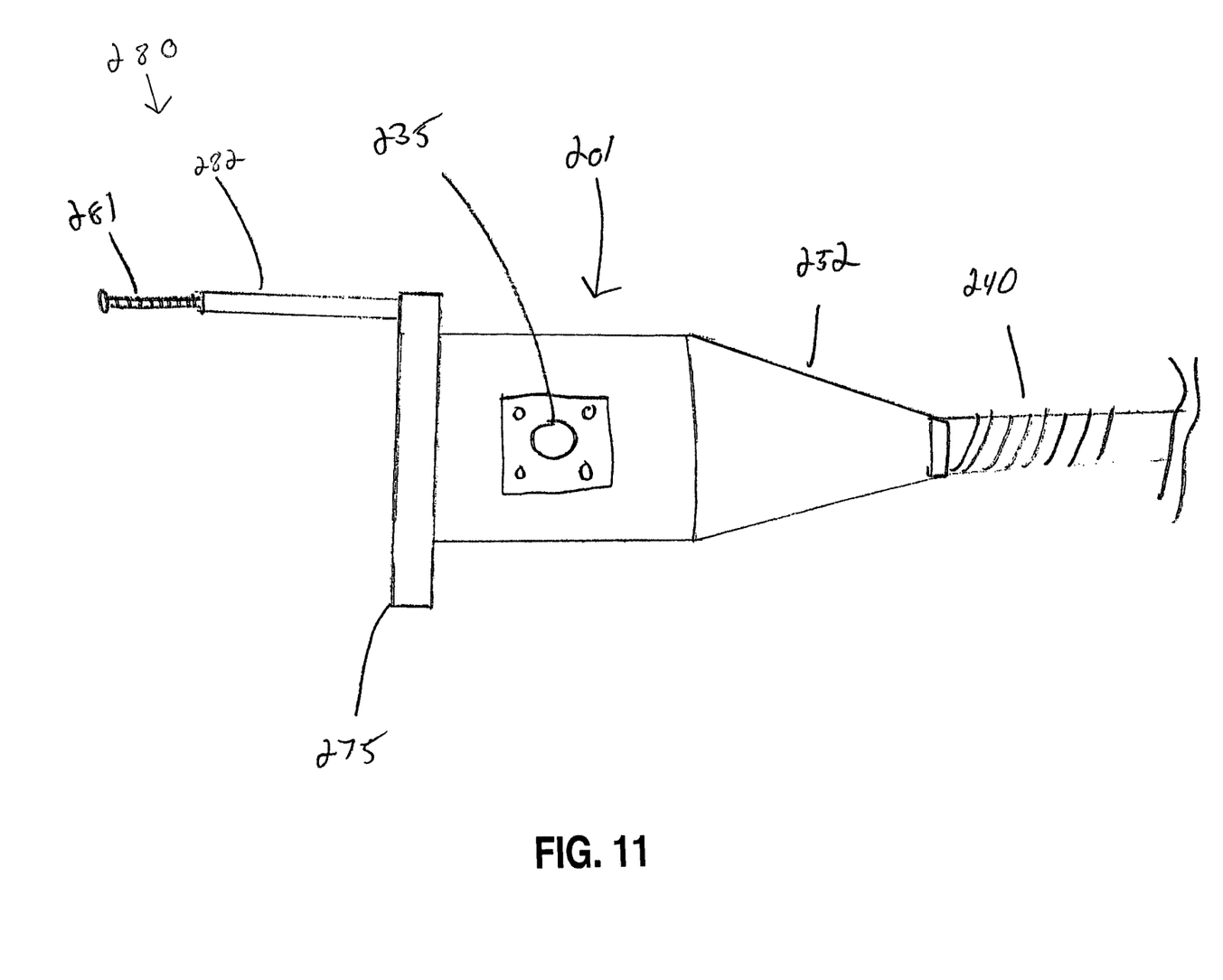
FIG. 11 is large scale side view of a light emitting element according to one embodiment of the invention.

FIG. 11 shows a large scale view of another embodiment of light emitting element 201 including hand guide 275 and distance control element 280. Hand guide 275 preferably is configured to prevent a user's control hand from entering the path of the light radiation being emitted from the light emitting element. Hand guide 275 can be made from at least one material that either reflects, absorbs or transmits light, or from a combination of materials that have a combination of a light reflecting, absorbing or transmitting characteristics.

Distance control element 280 is structured and arranged to maintain a predetermined distance between the light emitting element 201 and the target surface of area on a patient. In one embodiment, distance control element 280 includes an adjustable spot size, such as but not limited to, a screw and threaded portion, where manipulation of the screw will selectively increase or decrease the distance between the light emitting element and the target surface area, thereby selectively increasing or decreasing the spot size painted onto the target surface area. As the embodiment of distance control element 280 applying a screw 281 and threaded portion 282 may come into limited contact with the target surface area, distance control element 280 is preferably made of a material not conducive to exacerbating a wound at or near the target surface area. Preferably light emitting element 201, and system 1 in general, is operated by a skilled technician with the necessary dexterity and hand eye coordination to avoid unnecessary contact with the target surface area while achieving a desired power surface energy to promote photobiostimulation at the intended treatment area.

In another embodiment distance control element 280 is electronically linked to microprocessor control 10. In this embodiment distance control element 280 may transmit a signal in real time to microprocessor control 10, which signal is indicative of the distance between the light emitting element 201 and the target surface area, where the microprocessor control 10 may automatically adjust the various operative parameters of system 1. Such operative parameters can include the power settings of the laser sources 160 and 170, the selected wavelength, the patient data, the treatment time, the target surface area, and the shape, size and pattern of the light radiation directed at the target surface area. Optionally microprocessor control 10 also selectively adjusts and control lens 260 and focus alignment disk 258 in order to direct an appropriate amount of light radiation at the target surface area to achieve an optimum power energy density. Use of an iris type lens 260 has been found beneficial with patients that are restless, such as children. Iris type lens 260 can be electronically linked with the distance control element 280 and the microprocessor control 10 to simultaneously open and close the iris with the movements of the patient to maintain a consistent beam diameter.

In still another embodiment, distance control element 280 is a light sensing element or optical detector. In this embodiment distance control element detects light radiation reflecting off of the target surface area to determine the distance between the light emitting element 201 and the target surface area. Preferably, in this embodiment microprocessor control 10 will receive a signal from distance control element 280 indicative of the distance between the light emitting element 201 and the target surface area, where, as discussed above, microprocessor control 10 can control and adjust the various operation parameters of system 1 in order to provide an optimum power energy density at the intended treatment area. As an additional safety feature, the distance control element 280 of this embodiment can be structured and arranged to determine maximum and minimum allowed distances between light emitting element 201 and the target surface area. If light emitting element 201 is too far from the target surface area system 1 can be automatically shut down. This will prevent light emitting element 280 from being directed onto an unintended surface or in the case of a misalignment, preventing the emitted light radiation from entering the eye of a user, the patient or others that may be in the treatment room. Additionally, if light emitting element 201 is too close to the target surface area, system 1 can likewise be shut down to prevent thermal damage of the intended treatment area and the target surface area, if they differ.

In yet another embodiment, a light emitting element 201 may be a wrap containing multiple fibers can be connected to the system 1 effectively delivering hundreds of beams of light radiation to a large surface area. The wrap of this embodiment may contain a matrix of small apertures, each with a corresponding optical fiber. All of the fibers may converge into a single cable that may be releasably connected to either light emitting element 201 or directly to front panel 105.

In still other embodiments, light emitting element 201 may be controlled automatically by a robotics system capable of maneuvering element 201 in order to direct the proper amount of light radiation onto the target surface in order to promote photobiostimulation. There are many conventional robotics systems having linear stepper motors which can be utilized to automatically "dither" light emitting element 201 in a predetermined pattern to achieve the desired results.

Figure 12:
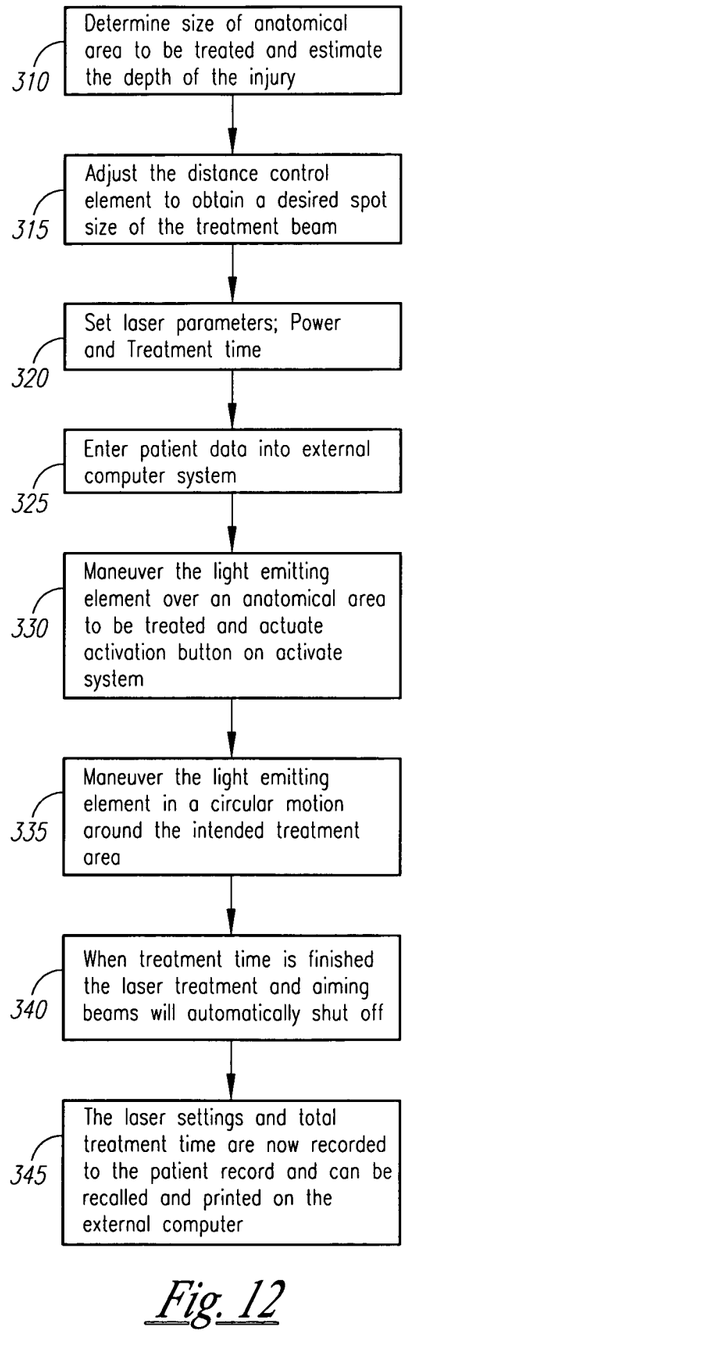
FIGS. 12 and 13 are general functional descriptions of the methods of operation of the apparatus according to one embodiment of the invention.

Referring now to FIG. 12, there is shown a functional description of the method of operation of system 1 according to one embodiment of the invention. At step 310 a user determines the size of anatomical area to be treated and estimates the depth of the injury. This step is provided to establish the proper power density as the more extensive the injury the greater dosage (time) required and the greater power that will be required. At step 315 a user may adjust the distance control element to obtain a desired spot size of the treatment beam such that it covers a substantial portion of an intended treatment area. A spot size chart may be included in the a user manual to assist the user with setting the proper spot size. As discussed above, a red aiming beam overlaps the infrared beam such that the red beam indicates exactly the location, size and shape of treatment beam as directed onto the target surface area.

At step 320 the user may set the various operation parameters of the laser including power and treatment time. At step 325 the user may enter patient data into either a microprocessor 10 or an external computer. It is understood that that system 1 can be linked to any of a variety of patient databases in a number of ways known in the art, such as direct PC link, internet, intranet, telephony, Ethernet, infrared or radio frequency. It will be understood that reference to microprocessor control 10 may include external databases via networking or other conventional linking as described herein. Such patent data can include patient name, address, social security number, insurance number, phone number, date of treatment, diagnosis notes, etc.

At step 330 the user may maneuver light emitting element 201 over an anatomical area to be treated and actuate activation button 235 to activate system 1. When switch 235 is actuated a data string may be sent from the light emitting element 201 to the microprocessor control 10 to record the setting with the patient name. At step 335 the user, or an automated system, may maneuver the light emitting element 201 in a circular motion around the intended treatment area. Movement of the light emitting element 201 around an entire injured area minimizes thermal accumulation created by absorption of the laser light. The freedom of motion with the non-contact method ensures thorough treatment. At step 340, system 1 can be programmed to shut down when the scheduled treatment period expires. The aiming beam indicates that the infrared beam is active, and when the aiming beam is deactivated the user knows that the treatment beam, which is preferably invisible infrared, is also deactivated.

At step 345 the user can store the system settings and total treatment time to the patient record, which information can be recalled and viewed and printed on an external computer. Optionally, the system automatically downloads treatment information to the patient database and updates the records. This information can be used for billing purposes as well as for data collection for clinical studies and medical legal issues.

Figure 13:
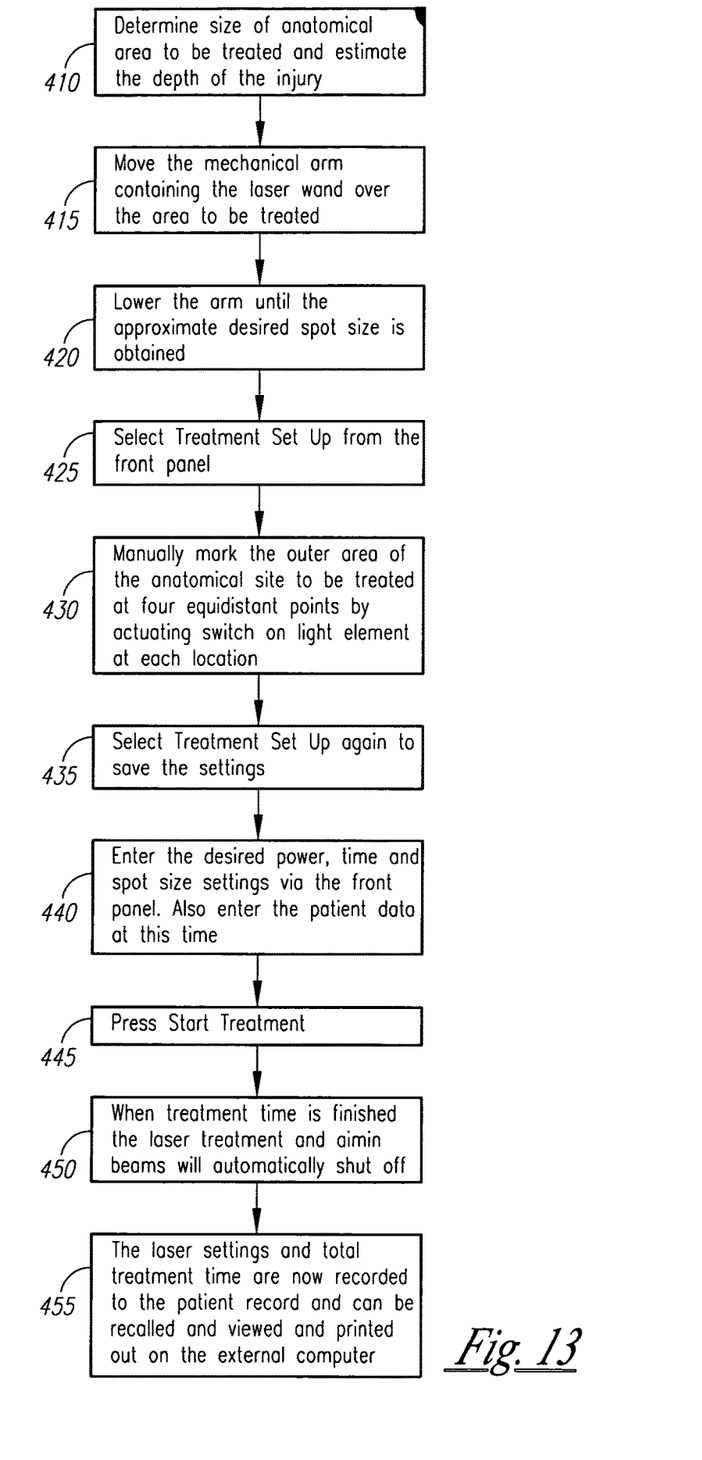

Referring now to FIG. 13, there is shown a functional description of the method of operation of system 1 according to another embodiment of the invention. At step 410, like step 310, a user determines the size of anatomical area to be treated and estimates the depth of the injury. At step 415, the user may maneuver a mechanical arm connected to light emitting element 201 over the area to be treated. At step 420 the user may maneuver the mechanical arm until an approximate desired spot size is obtained on the target surface area. The user may adjust the spot size to the proper setting based on information either manually entered via the front panel controls, or automatically uploaded via the patient database. The user may also set a range of operation for the mechanical arm. The visible red aiming beam is synchronized with and overlaps the infrared beam such that the red beam indicates exactly the location, size and shape of the treatment beam over the target surface area.

At step 430 the user may select treatment set up information from the front panel 105. To calibrate and set the system, at step 435 the user may manually mark the outer area of the anatomical site to be treated at four equidistant points by actuating switch button 235 on light emitting element 201 at each location to mark it. The light emitting element, can be attached to the mechanical arm capable of moving in the X, Y and Z plains, contains a detector, which registers the distance from the anatomical area. When switch button 235 is actuated a position of the mechanical arm can be recorded and when marked in four spots the target surface area may be mapped out. User set up provides data points reflective of the settings. If the patient moves the mechanical arm may automatically adjust accordingly to maintain the recorder X, Y, Z settings. As a safety feature, a dramatic shift by the patient, or malfunction by the mechanical arm, will cause the system to shut down.

At step 440 the user may enter the desired power, time and spot size settings via the front panel. Also entered at this time is the patient data described above. At step 445 the user starts the automatic treatment period. When the start button is actuated a data string may be sent from the light emitting element 201 to the microprocessor 10 or other database to record the settings with the patient data. The mechanical arm may move light emitting element 201 across the target surface area in a predetermined pattern designed for the most effective treatment of the intended treatment area. The motion of the light emitting element 201 is such that it is maneuvered around the entire intended treatment area and therefore minimizes thermal component created by absorption of the laser light.

At step 450 the treatment is complete and the system is shut down. As describe above the aiming beam is deactivated which informs the user that the invisible infrared treatment beam has been deactivated.

At step 455, the settings and total treatment time are now recorded to the patient record and can be recalled and viewed and printed on the external computer. This information can be used for billing purposes as well as for data collection for clinical studies and medical legal issue.

For the convenience of the reader, the above description has focused on a representative sample of all possible embodiments, a sample that teaches the principles of the invention and conveys the best mode contemplated for carrying it out. The description has not attempted to exhaustively enumerate all possible variations. Further undescribed alternative embodiments are possible. It will be appreciated that many of those undescribed embodiments are within the literal scope of the following claims, and others are equivalent.

What is claimed is:

1. A photobiostimulation device for applying light radiation to a target surface area of a patient in order to create a selected power density at or below the target surface area to aid in the recovery of damaged cells without further damaging the cells said device comprising:
   at least one laser source;
   a light emitting element, in optical communication with the at least one laser source and capable of directing a divergent beam of laser light for a predetermined amount of time up to 7200 seconds on a target surface area of a patient; and
   a control element operably connected to the light emitting element adapted to control a distance between the light emitting element and the target surface area to maintain selected power density.

2. The photobiostimulation device according to claim 1 further comprising a hand guide element connected to the light emitting element.

3. The photobiostimulation device according to claim 2, wherein at least a portion of the hand guide is made of a translucent material.

4. The photobiostimulation device according to claim 2, wherein the control element comprises a light sensing element, the light sensing element sensing light reflected from light waves directed on the target surface area and sending a distance signal to a processor.

5. The photobiostimulation device according to claim 2, wherein the control element comprises a spot size adjuster releasably connected to the light emitting element.

6. The photobiostimulation device according to claim 5, where the spot size adjuster comprises a threaded portion and an adjustable screw, where manipulation of the screw selectively maintains the distance between the target surface area and the light emitting element, effectively controlling a spot size of the divergent beam of laser light.

7. The photobiostimulation device according to claim 2, where the light emitting element further comprises a focusing element, the focusing element adapted to focus the divergent beam of laser light onto the target surface area.

8. The photobiostimulation device according to claim 7, where the focusing element comprises a lens.

9. The photobiostimulation device according to claim 8 where the focusing element comprises a shutter.

10. The photobiostimulation device according to claim 8, where the lens is optically coated.

11. The photobiostimulation device according to claim 10, where the lens is a collimating lens.

12. The photobiostimulation device of claim 1, wherein said at least one laser source comprises a laser adapted for delivering the divergent beam of laser light, having the selected power density, over a wide surface area without thermally damaging the target surface area of the patient.

13. The photobiostimulation device of claim 1, wherein the at least one laser source is capable of creating laser light in the infrared spectrum and delivering the laser light to the light emitting element.

14. The photobiostimulation device of claim 13, wherein the at least one laser source comprises two laser sources including one visible spectrum laser source optically connected to said light emitting element, the visible spectrum laser source being capable of creating visible light and delivering the visible light to said light emitting element.

15. The photobiostimulation device of claim 14, wherein said laser light is in the red visible spectrum.

16. The photobiostimulation device of claim 15, wherein the selected power density of the light radiation at said target surface area on the skin of the patient is between about 50 mW/cm$^2$ and 25,000 mW/cm$^2$.

17. The photobiostimulation device of claim 16, wherein said divergent beam of laser light is a pulsed wave.

18. The photobiostimulation device of claim 1, wherein divergent beam of laser light casts a spot size defining a circle having a diameter between about 0.5 cm and 10 cm.

19. The photobiostimulation device of claim 18, wherein said divergent beam of laser light is a pulsed wave.

20. The photobiostimulation device of claim 1, wherein said divergent beam of laser light is capable of being emitting in a pulsed wave.

21. The photobiostimulation device of claim 1, wherein the light emitting element further comprises a wrap containing a matrix of apertures each aperture having an optical fiber in optical communication with the at least one laser source.

22. A system for photobiostimulation of a target surface area of a patient, where the target surface area is located on the skin of the patient, the system comprising:
  a microprocessor controller;
  a unified portable housing having a power supply connected to said microprocessor controller and at least two laser power sources capable of simultaneously generating different selected wavelengths of laser light;
  an optical cable optically connected to the at least two laser light power sources, the optical cable capable of simultaneously transmitting the different selected wavelengths of laser light;
  a light emitting element optically connected to the optical cable and linked to the microprocessor controller, the light emitting element comprising a switch operable by a single hand of a user, the switch being operable to actuate the light emitting element to simultaneously emit the different selected wavelengths of laser light directed onto the target surface area in a spot size having a diameter of between about 0.5 cm and about 10 cm; and
  a distance control element operably linked to the light emitting element and the microprocessor controller, to maintain an optimum power density on the target surface area in a controllable and calculable manner such that power density remains constant despite changes in distance between the light emitting element and the target surface area;
  wherein, the microprocessor controller is programmed to determine the distance between the light emitting element and the target surface area and based on the distance between the light emitting element and the target surface control and selectively modify one or more of the power of the different selected wavelengths of laser light, the wavelength of one of the different selected wavelengths of laser light, a treatment time of the target surface area, or the spot size in order to maintain the optimum power density on the target surface area of between about 50 mW/cm$^2$ and about 25,000 mW/cm$^2$.

* * * * *